US011365217B2

(12) United States Patent
Liu

(10) Patent No.: US 11,365,217 B2
(45) Date of Patent: Jun. 21, 2022

(54) PEPTIDES FOR TREATING TELOMERE DYSFUNCTION-ASSOCIATED DISEASES AND USES THEREOF

(71) Applicants: HANGZHOU DUANLI BIOTECHNOLOGY COMPANY LIMITED, Zhejiang (CN); Dan Chen, Zhejiang (CN)

(72) Inventor: Jun-Ping Liu, Zhejiang (CN)

(73) Assignees: HANGZHOU DUANLI BIOTECHNOLOGY COMPANY LIMITED, Hangzhou (CN); Dan Chen, Hangzhou (CN)

( * ) Notice: Subject to any disclaimer, the term of this patent is extended or adjusted under 35 U.S.C. 154(b) by 45 days.

(21) Appl. No.: 16/921,912

(22) Filed: Jul. 6, 2020

(65) Prior Publication Data

US 2021/0040152 A1    Feb. 11, 2021

Related U.S. Application Data

(63) Continuation of application No. PCT/CN2018/124178, filed on Dec. 27, 2018.

(30) Foreign Application Priority Data

Jan. 5, 2018  (CN) .......................... 201810009703.9

(51) Int. Cl.
| | |
|---|---|
| *A61K 38/00* | (2006.01) |
| *C07K 7/06* | (2006.01) |
| *A61P 1/16* | (2006.01) |
| *A61P 11/00* | (2006.01) |

(52) U.S. Cl.
CPC .................. *C07K 7/06* (2013.01); *A61P 1/16* (2018.01); *A61P 11/00* (2018.01); *A61K 38/00* (2013.01)

(58) Field of Classification Search
None
See application file for complete search history.

(56) References Cited

U.S. PATENT DOCUMENTS

| | | |
|---|---|---|
| 7,279,328 B1 | 10/2007 | Andrews et al. |
| 2002/0193289 A1 | 12/2002 | Andrews |
| 2003/0225027 A1 | 12/2003 | Huang |

FOREIGN PATENT DOCUMENTS

| | | |
|---|---|---|
| CN | 1575300 A | 2/2005 |
| CN | 102311493 A | 1/2012 |
| WO | 2011079431 A1 | 7/2011 |

OTHER PUBLICATIONS

Wermuth, et al "Glossary of Terms used in Medicinal Chemistry," Pure and Appl. Chem., vol. 70, No. 5, pp. 1129-1143, (1998) (Year: 1998).*

* cited by examiner

*Primary Examiner* — Thomas S Heard

(57) ABSTRACT

Disclosed herein is a peptide for inhibiting telomere damage, where the peptide is ST8 (SEQ ID NO:25), or an analogue such as retro-inverso peptide (reversed, inversed in dextral amino acid) or derivative (SEQ ID NO: 1, 19 or 20) thereof. This application further provides applications of the peptide in the treatment of telomere dysfunction-associated diseases and in the anti-aging of bone marrow tissues.

7 Claims, 18 Drawing Sheets

Specification includes a Sequence Listing.

PEPTIDES FOR TREATING TELOMERE DYSFUNCTION-ASSOCIATED DISEASES AND USES THEREOF

CROSS REFERENCE TO RELATED APPLICATIONS

This application is a continuation of International Patent Application No. PCT/CN2018/124178, filed on Dec. 27, 2018, which claims the benefit of priority from Chinese Patent Application No. 201810009703.9, filed on Jan 5, 2018. The content of the aforementioned application, including any intervening amendments thereto, is incorporated herein by reference in its entirety.

REFERENCE TO AN ELECTRONIC SEQUENCE LISTING

The contents of the electronic sequence listing (Sequence-Listing-2020-11-01.txt; Size: 8,000 bytes; and Date of Creation: Nov. 1, 2020) is herein incorporated by reference in its entirety.

TECHNICAL FIELD

This application relates to biotechnology, and more particularly to a peptide for treating telomere dysfunction-associated diseases and uses thereof.

BACKGROUND

Chromosomal telomere DNA damage causes cellular senescence which in turn causes senescence-associated chronic diseases, such as pulmonary fibrosis, liver fibrosis and skin fibrotic lesions. The shortened or dysfunctional telomeres are widely recognized as causes of cellular senescence. Stress such as radiation, chemical substances (e.g., antibiotics) and reactive oxidative species will exacerbate the shortening and damage of telomeres to further give rise to premature aging. However, the mechanism that the stress causes the shortening and damage of telomeres to further result in premature aging and diseases associated therewith has remained largely unknown for decades. Among the premature aging-related diseases, the causes of idiopathic pulmonary fibrosis (IPF) and dyskeratosis congenita (DC) are also unclear, and there are no effective drugs for the clinical treatment of these diseases.

Irradiation stress, oxidative stress and DNA damage-associated drugs such as bleomycin have been demonstrated to cause pulmonary fibrosis and the telomere shortening, but the specific mechanism is still unclear. It has been interestingly found that different stresses can activate the E3 ubiquitin ligase FBW7 (F-box and WD40 repeat domain-containing 7, also termed FBW7, Sel-10, hCDC4, or hAgo), which can act as a substrate recognition component to promote the targeted degradation of substrate proteins including oncoproteins such as c-myc, n-myc, Notch, Cyclin E, c-Jun, Aurora-A and mTOR. In mice, the loss of FBW7 function will activate the expansion of stem cells, and FBW7 has been found to be subjective to mutations in many kinds of human tumors. However, the inhibitory effect of FBW7 on cell proliferation has not been fully understood.

The telomere binding protein TPP1 is an important component in a protein complex called shelterin for capping the telomere DNA, and mutations in the ACD gene encoding TPP1 are associated with aging-related diseases such as dyskeratosis congenital and bone marrow failure. Since telomere damage, including telomere shortening and telomere dysfunction, will raise DNA damage response (DDR) to accelerate the aging process, it is a primary cause of the aging-related diseases. The aging-related diseases that have been reported to be closely associated with telomere dysfunction include chronic obstructive pulmonary diseases (COPD), IPF, DC, and other fibrous tissue proliferative diseases, liver fibrosis, bone marrow stem cell reduction, anemia, immune dysfunction, thymic fibrosis, ovarian fibrosis, premature ovarian failure (POF), fibrosis of bone and joint, osteoporosis, vascular fibrosis, arteriosclerosis, heart disease, renal fibrosis, neurodegenerative injury and disease, diabetes, skin aging such as dyskeratosis, and tumors (Science, 350: 1193-8, 2015; Clin Sci (Lond). 120(10):427-40, 2011). For example, lung aging is an important risk factor leading to pulmonary fibrosis, and among the pulmonary fibrosis, IPF has highest mortality. It has been observed under the occurrence of IPF that a reduction occurs in the telomere length, and the replication, proliferation and differentiation of alveolar epithelial stem cells are inhibited.

SUMMARY

Given the above, an object of this application is to provide a peptide for inhibiting telomere damage, and variants and derivatives thereof, and an application thereof in the treatment of telomere damage-associated diseases, where the peptide is artificially designed and synthesized in vitro based on the amino acid sequence of FBW7. The peptide is named telomere dysfunction inhibitor (TELODIN) herein.

Technical solutions of the invention are described as follows.

In a first aspect, this application provides a peptide for inhibiting telomere damage, or an analogue or derivative thereof, wherein the peptide is ST8 (SEQ ID NO:25).

In an embodiment, the analogue is DST8 (SerArgAsnGlyThrGluGluThr, in D or dextral amino acids); and the derivative is YK21 (SEQ ID NO:1), DYK21 (SEQ ID NO:19, in D-amino acids) or DKY21 (SEQ ID NO:20, in D-amino acids).

In an embodiment, the ST8 has a molecular weight of 892.88; the DST8 has a molecular weight of 892.88; the YK21 has a molecular weight of 2619.96; the DYK21 a molecular weight of 2619.94; and the DKY21 has a molecular weight of 2619.96.

In a second aspect, this application provides a method for treating a telomere dysfunction-associated disease in a patient in need thereof, comprising:

administering any one of the above peptides to the patient.

In an embodiment, the telomere dysfunction-associated disease is a disease caused by telomere damage or telomere shortening, and the disease caused by telomere damage or telomere shortening is selected from the group consisting of pulmonary fibrosis, myocardial fibrosis, liver fibrosis, renal fibrosis, bone marrow fibrosis, hematopoietic stem cell reduction, anemia, immune dysfunction, thymic fibrosis, ovarian fibrosis, premature ovarian failure, bone and joint fibrosis, osteoporosis, vascular fibrosis, neurodegenerative damage, diabetes, premature aging and degeneration of tissues and organs, tumors and age-related chronic obstructive pulmonary disease.

In an embodiment, the aging of tissues and organs comprises skin premature aging comprising skin fibrotic lesion, skin wrinkles, dyskeratosis, hair follicle and regeneration disorders, and hair loss and alopecia.

In an embodiment, the telomere damage leading to the premature aging and degeneration of tissues and organs, pulmonary fibrosis, myocardial fibrosis, liver fibrosis, renal fibrosis, bone marrow fibrosis, thymic fibrosis, ovarian fibrosis, bone and joint fibrosis, vascular fibrosis, and skin fibrosis is induced by environmental stress.

In a third aspect, this application also provides a method for postponing the aging of bone marrow tissues, comprising:

administering any one of the above peptides to a subject in need.

It has been found that the above peptides are all derived from the carbon-terminal amino acid sequence of FBW7, i.e., $^{687}$GSRNGTEETK, which indicates the carbon-terminal amino acid sequence of FBW7 has an activity of inhibiting the telomere damage, and any peptides derived from the carbon-terminal amino acid sequence of FBW7 and analogues and derivatives thereof all have the potential to inhibit the telomere damage.

It has been demonstrated that the above peptides all are capable of affecting the telomere damage, which indicates that the modification products and derivatives thereof have the potential to treat the diseases caused by telomere damage, especially the aging-related diseases. For example, the intratracheal administration of YK21 (SEQ ID NO:1) to mice in one time can improve the lung respiratory function, prevent lung respiratory dysfunction caused by stress, prevent the lung aging damage and pulmonary fibrosis, extend telomere length and increase the number of lung stem cells; the similar effects can also be obtained through the one-time organ administration of ST8 (SEQ ID NO:25) to mice.

In addition to the use in the prevention and treatment of pulmonary fibrosis caused by stress, the above-mentioned peptides can also be applied to the prevention and treatment of liver fibrosis, skin damage and aging-related diseases caused by stress. For example, the application of DYK21 (SEQ ID NO:19, in D-amino acids) to the dorsal skin of mice can raise a significant increase in the number of dermal stem cells and hair follicles. Under the irradiation of X rays, the mice in the control group experience significant skin thickening and fibrosis, and proliferation of a large number of fibrous tissues in the dermis. By comparison, the mouse skins coated with DYK21 have resistance to the X ray-induced skin fibrosis, and are completely free of skin fibrosis caused by radiation. In addition, the intraperitoneal injection of DST8 can prevent the liver fibrosis caused by carbon tetrachloride drugs.

The application of the peptide provided herein to the prevention and treatment of telomere damage in normal state and stress state reveals that the peptide can effectively prevent the telomere shortening, promote the proliferation of stem cells, improve the lung respiratory function, increase the number of skin hair follicles, and extend the lifespan of mice under stress. Therefore, the peptide provided herein has an anti-aging activity, specifically in the resistance to the aging of organs and tissues including lung, skin, liver, brain, heart and bone marrow.

The application of the peptide provided herein to the prevention and treatment of telomere damage and shortening in normal state and stress state reveals that the peptide can extend the telomere lengths, promote the proliferation of stem cells and prevent lung and skin aging-related diseases caused by stress. Therefore, the peptide has the potential to treat other diseases caused by telomere damage and shortening, including liver fibrosis such as cirrhosis, myocardial fibrosis, renal fibrosis, bone marrow fibrosis, hematopoietic stem cell reduction, anemia, thymus fibrosis, immune dysfunction, ovarian fibrosis, premature ovarian failure, bone and joint fibrosis, osteoporosis, vascular fibrosis and neurodegenerative injury.

BRIEF DESCRIPTION OF THE DRAWINGS

FIGS. 1A-D illustrate effect of various peptides on telomere DNA damage in Hela cells under irradiation. FIG. 1E illustrates time schedule of intratracheal administration of drugs to mice exposed to bleomycin. FIGS. 1F-H: expiratory influx, tidal and minute ventilation volumes in bleomycin-induced mice that were respectively perfused with YK21 (SEQ ID NO:1) and control peptide YK21h (SEQ ID NO:2). FIG. 1I: hydroxyproline level in lung tissues of bleomycin-induced mice that were respectively perfused with YK21 and control peptide YK21h. FIG. 1J: Masson and H&E staining results and expression of α-SMA in bleomycin-induced mice that were respectively perfused with YK21 and control peptide YK21h. FIGS. 1K-L: relative expression levels of SPC and TPP1 and telomere fluorescence intensity in bleomycin-induced mice that were respectively perfused with YK21 and control peptide YK21h.

FIGS. 2A-2C: expiratory influx, tidal and minute ventilation volumes in bleomycin-induced mice respectively perfused with ST8 and control peptide GE8 (SEQ ID NO:24). FIG. 2P illustrates the relative expression level of α-SMA, Col6αand MMP3 in mice that were inoculated with FBW7 lentiviruses and respectively perfused with YK21 and YK21h.

FIG. 3A: body weight of mice respectively treated with DYK21 and control peptide DCTL1 (SEQ ID NO:27, AlaCysThrGlySerThrGlnHisGlnCysGlyGlyGlyGlySerArgAsnGlyThrGluGluThr). FIGS. 3B-C: H&E staining and Masson staining results of mice respectively treated with DYK21 and DCTL1. FIGS. 3D-G: the number of hair follicles, proportion of area of fibrosis, body weight and life span of mice respectively treated with DYK21 and DCTL1 under X-ray irradiation.

DETAILED DESCRIPTION OF EMBODIMENTS

Figure 1A:
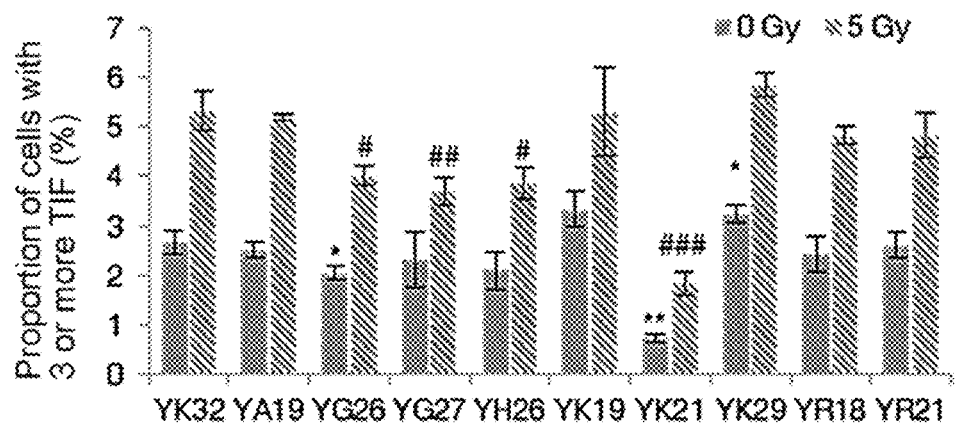
FIGS. 1A-L show inhibitory effect of TELODIN peptides on telomere damage and pulmonary fibrosis.

This application will be described in detail below with reference to the accompanying drawings and embodiments. It should be understood that these embodiments are merely illustrative of the application, and are not intended to limit the application. Unless otherwise specified, the experiments below are carried out under conventional conditions or as instructed by manufacturer. Unless otherwise specified, the reagents and instruments used in the following embodiments are all commercially available.

Definition

As used herein, those peptide names with a starting letter of "D" indicate that these peptides are synthesized from D-amino acids.

EXAMPLE 1

Inhibition of TELODIN Peptides on Telomere Damage

Human cervical carcinoma cells Hela were respectively treated with various peptides (as shown in SEQ ID NOs:1-26 in Table 1) for 4 h, and then the cells treated with the same peptide were divided into two groups, which were respectively subjected to 0-Gy and 5-Gy irradiation of X ray for 1 h and detected for telomere DNA damage using fluorescence in situ hybridization (FISH). The results were shown in FIGS. 1A-1D.

TABLE 1

TELODIN peptides

| SEQ ID No. | Name | Sequences |
|---|---|---|
| 1 | YK21 (TELODIN) | TyrGlyArgLysLysArgArgGluArg ArgArgGlySerArgAsnGlyThrGlu GluThrLys |
| 2 | YK21h | TyrGlyArgLysLysArgArgGluArg ArgArgGlyGluArgAsnGlyThrGlu GluThrLys |
| 3 | YK32 | TyrGlyArgLysLysArgArgGluArg ArgArgGlySerArgAsnGlyThrGlu GluThrLysLeuLeuValLeuAspPhe AspValAspMetLys |
| 4 | YG26 (TELODIN) | TyrGlyArgLysLysArgArgGluArg ArgArgGlySerThrAspArgThrLeu LysValTrpAsnAlaGluThrGly |
| 5 | YH26 (TELODIN) | TyrGlyArgLysLysArgArgGluArg ArgArgGlyGluLeuLysSerProLys ValLeuLysGlyHisAspAspHis |
| 6 | YA19 | TyrGlyArgLysLysArgArgGluArg ArgArgGlyProAsnLysHisGlnSer Ala |
| 7 | YG27 (TELODIN) | TyrGlyArgLysLysArgArgGluArg ArgArgAlaValThrGlyLysCysLeu ArgThrLeuValGlyHisThrGlyGly |
| 8 | YK19 | TyrGlyArgLysLysArgArgGluArg ArgArgGlyAlaTyrAspPheMetVal Lys |

TABLE 1-continued

TELODIN peptides

| SEQ ID No. | Name | Sequences |
|---|---|---|
| 9 | YK29 | TyrGlyArgLysLysArgArgGluArg ArgArgLysGluGluGlyIleAspGlu ProLeuHisIleLysArgArgLysVal IleLys |
| 10 | YR18 | TyrGlyArgLysLysArgArgGluArg ArgArgGlyHisThrSerThrValArg |
| 11 | YR21 | TyrGlyArgLysLysArgArgGluArg ArgArgLysArgArgArgThrGlyGly SerLerArg |
| 12 | YK21a (TELODIN) | TyrGlyArgLysLysArgArgGluArg ArgArgArgAsnGlyThrGluGluThr Lys |
| 13 | YK21b | TyrGlyArgLysLysArgArgGluArg ArgArgGlySerAsnGlyThrGluGlu ThrLys |
| 14 | YK21c (TELODIN) | TyrGlyArgLysLysArgArgGluArg ArgArgGlySerArgGlyThrGluGlu ThrLys |
| 15 | YK21d | TyrGlyArgLysLysArgArgGluArg ArgArgGlySerArgAsnGlyThrGlu GluThr |
| 16 | YK21e | TyrGlyArgLysLysArgArgGluArg ArgArgGlySerArgAsnGlyThrGlu Glu |
| 17 | YK21f | TyrGlyArgLysLysArgArgGluArg ArgArgGlySerArgAsnGlyThrGlu ThrLys |
| 18 | YK21g | TyrGlyArgLysLysArgArgGluArg ArgArgGlyAspArgAsnGlyThrGlu GluThrLys |
| 19 | DYK21 (TELODIN) | TyrGlyArgLysLysArgArgGluArg ArgArgGlySerArgAsnGlyThrGlu GluThrLys |
| 20 | DKY21 (TELODIN) | LysThrGluGluThrGlyAsnArgSer GlyArgArgArgGlnArgArgLysLys ArgGlyTyr |
| 21 | KY21 (TELODIN) | LysThrGluGluThrGlyAsnArgSer GlyArgArgArgGlnArgArgLysLys ArgGlyTyr |
| 22 | GK10 (TELODIN) | GlySerArgAsnGlyThrGluGluThr Lys |
| 23 | GT9 (TELODIN) | GlySerArgAsnGlyThrGluGluThr |
| 24 | GE8 | GlySerArgAsnGlyThrGluGlu |
| 25 | ST8 (TELODIN) | SerArgAsnGlyThrGluGluThr |
| 26 | SE7 | SerArgAsnGlyThrGluGlu |

Figure 1B:
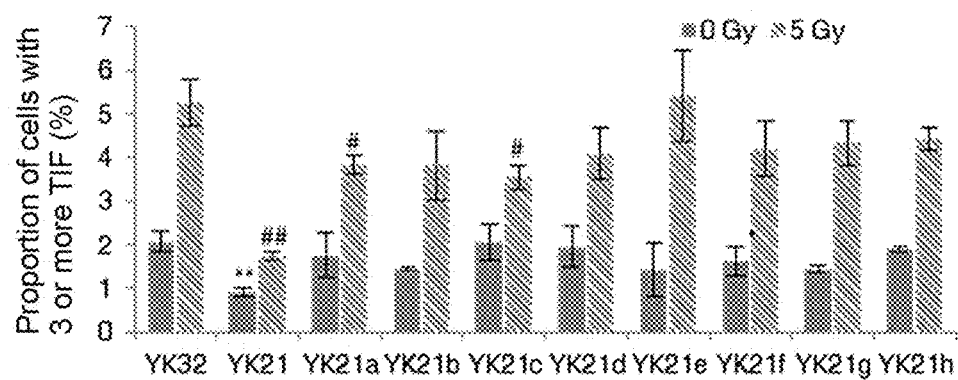
Figure 1C:
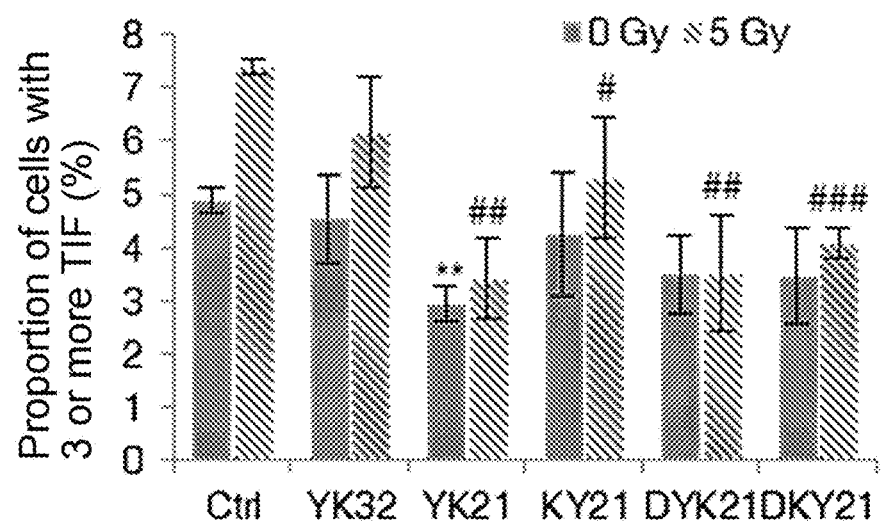
Figure 1D:
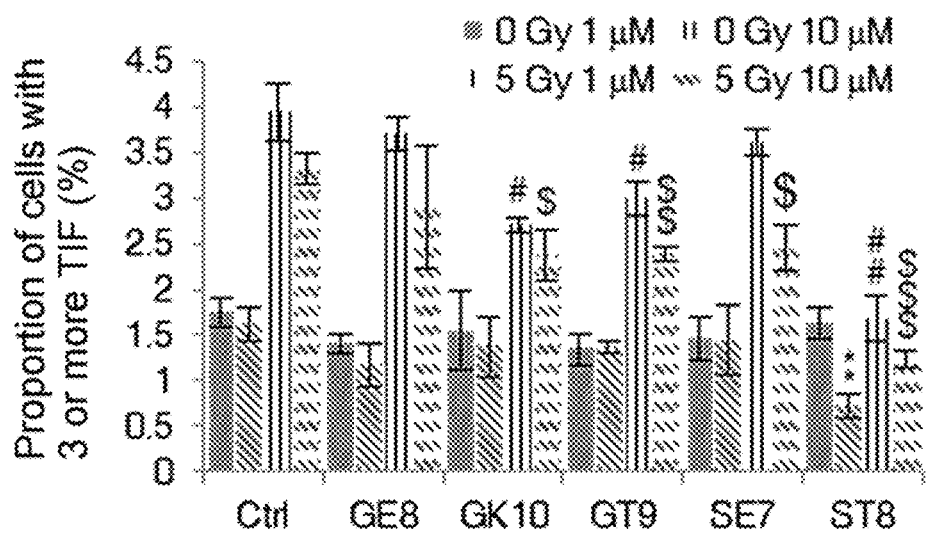

It was demonstrated by these figures that YK21, which was sequence dependent, can not only significantly reduce the telomere DNA damage at a basic level, but also completely inhibit the telomere DNA damage caused by irradiation (FIGS. 1A-B); DYK21 (SEQ ID NO:19) and DKY21 (SEQ ID NO:20), which were completely synthesized from D-amino acids, showed inhibitory effect on the telomere DNA damage caused by irradiation of X rays (FIG. 1C); and ST8, which was synthesized from 8 amino acids, was also capable of significantly inhibiting the telomere DNA damage caused by irradiation of X rays (FIG. 1D).

EXAMPLE 2

Figure 1E:
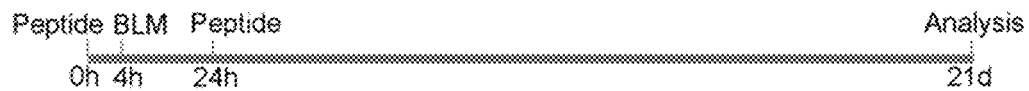

Inhibition of YK21 on Telomere Damage, Chronic Obstructive Pulmonary Diseases and Pulmonary Fibrosis 18 3-6 month old wild mice were equally divided into 6 groups, where 3 groups of mice were intratracheally perfused with YK21 (1 mg per kilogram of body weight), and the other 3 groups of mice were intratracheally perfused with YK21h (1 mg per kilogram of body weight) as control. The time program of this experiment was shown in FIG. 1E, specifically, 4 hours later, the mice were all intratracheally perfused with bleomycin (3 mg per kilogram of body weight), and 20 hours after the perfusion of bleomycin, two groups of mice were respectively received a second perfusion of YK21 and a second perfusion of YK21h. After 21 days of the first perfusion of peptide, the mice were all subjected to endotracheal intubation for the detection of respiratory function, and the lung tissue RNA was extracted and subjected to real-time quantitative PCR to detect the mRNA expression of TPP1 and SPC. The lung tissues were embedded with paraffin, sectioned, subjected to Masson and H&E staining and detected by immunofluorescence assay for the expression of α-SMA. Moreover, 10 mg of lung tissues were employed for the determination of hydroxyproline content; and the telomere length of alveolar epithelial type II stem cells (SPC+telomere probe) and the telomere DNA damage in lung tissues (53BP1+telomere probe) were detected by FISH.

Figure 1F:
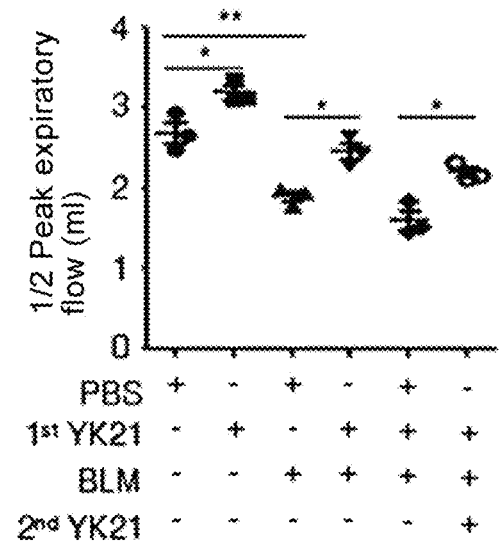
Figure 1G:
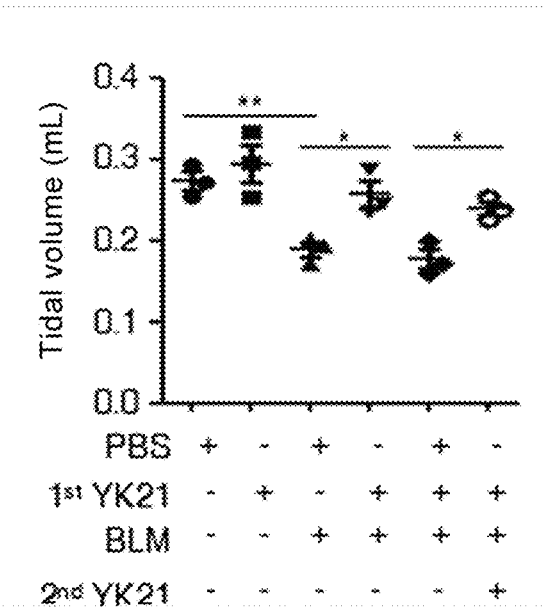
Figure 1H:
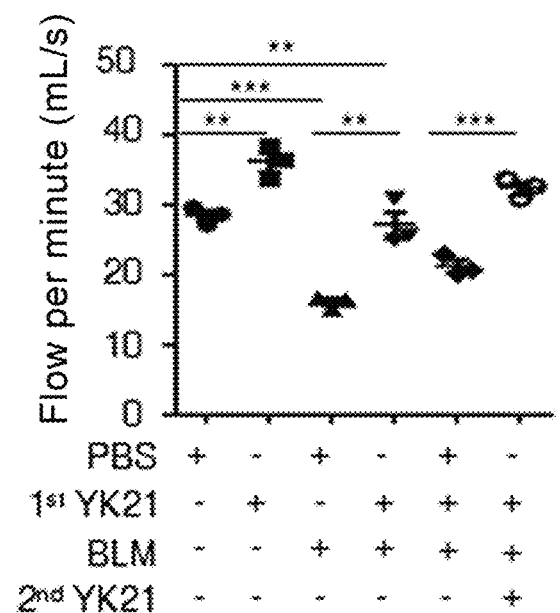
Figure 1I:
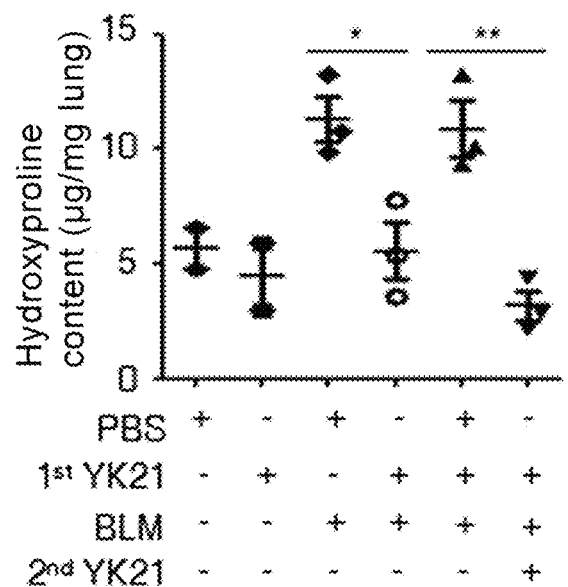
Figure 1J:
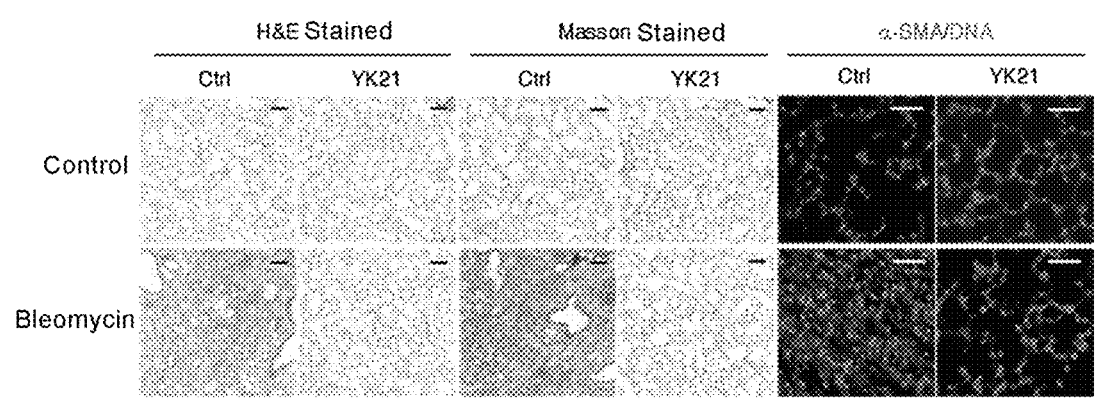
Figure 1K:
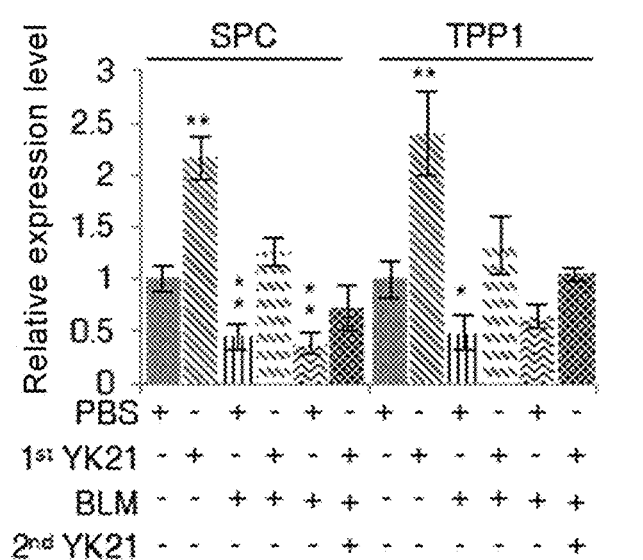
Figure 1L:
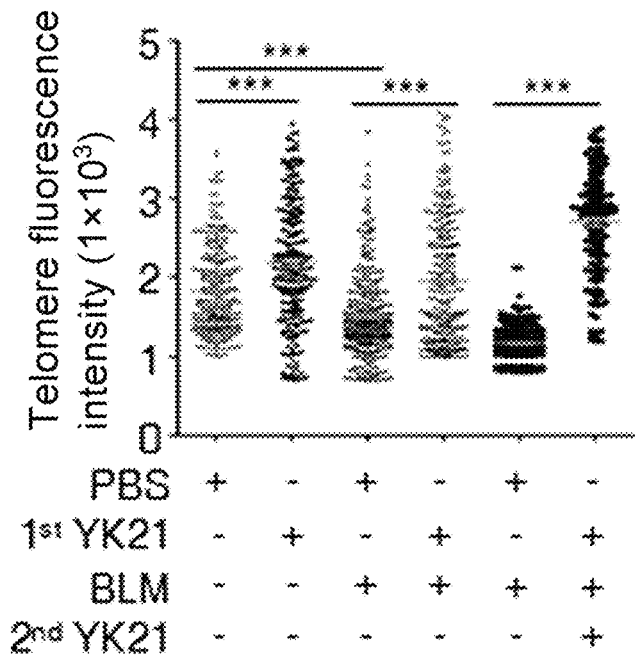

The results showed that compared to the control peptide YK21h, YK21 can not only significantly improve the respiratory function in mice (FIGS. 1F-H), but also inhibit the pulmonary fibrosis induced by bleomycin (FIGS. 1I-J). In addition, YK21 also led to an increase in the expression of TPP1 and SPC (FIG. 1K) and the telomere length of type II epithelial cells (FIG. 1L).

EXAMPLE 3

Inhibition of ST8 on Telomere Damage, Chronic Obstructive Pulmonary Diseases And Pulmonary Fibrosis Twelve 3-6 month old wild mice were equally divided into four groups, where two groups of mice were intratracheally perfused with ST8 (1 mg per kilogram of body weight) (SEQ ID NO:25), and the other two groups of mice were intratracheally perfused with GE8 (SEQ ID NO:24) as control (1 mg per kilogram of body weight). 4 hours later, the mice were all intratracheally perfused with bleomycin (3 mg per kilogram of body weight), and 21 days after the perfusion of peptide, the mice were subjected to endotracheal intubation for the detection of respiratory function. The type II cells were sorted by flow cytometry and calculated for the proportion. The lung tissue RNA was extracted and subjected to real-time quantitative PCR for the detection of mRNA expression of NG2, T1a, s100a4, α-SMA and Col6a, and the lung proteins were also extracted and detected by Western Blot for the expression of FBW7, TPP1, α-SMA and internal reference GAPDH. The lung tissues were embedded with paraffin, sectioned, subjected to Masson and H&E staining and detected by immunofluorescence assay for the expression of α-SMA. Moreover, 10 mg of lung tissues were employed for the determination of hydroxyproline content; and the telomere length of type II cells (SPC+telomere probe) was detected by FISH.

Another twelve 3-6 month old wild mice were equally divided into 4 groups, where two groups of mice were intratracheally perfused with ST8 (1 mg per kilogram of body weight), and the other two groups of mice were intratracheally perfused with GE8 as control (1 mg per kilogram of body weight). 4 hours later, the two groups of mice perfused with ST8 were respectively intratracheally perfused with a control- or FBW7-lentivirus, and the two groups of mice perfused with GE8 were also respectively intratracheally perfused with the control- or FBW7-lentiviruses. The perfusion was performed every other 4 days in a total number of 4. On the fourth day after the fourth perfusion, the mice were subjected to endotracheal intubation for the detection of respiratory function. The type II cells were sorted by flow cytometry and calculated for the proportion. The lung tissue RNA was extracted and subjected to real-time quantitative PCR for the detection of mRNA expression of α-SMA, Col6a, and MMP3, and the lung proteins were also extracted and detected by Western Blot for the expression of FBW7, TPP1, SPC, α-SMA and internal reference GAPDH. The lung tissues were embedded with paraffin, sectioned, subjected to Masson and H&E staining and detected by immunofluorescence assay for the expression of α-SMA. Moreover, the proportion of lung type II epithelial cells (SPC positive cells) was obtained by immunofluorescence assay; and the telomere length of type II cells (SPC+telomere probe) was detected by FISH.

Figure 2A:
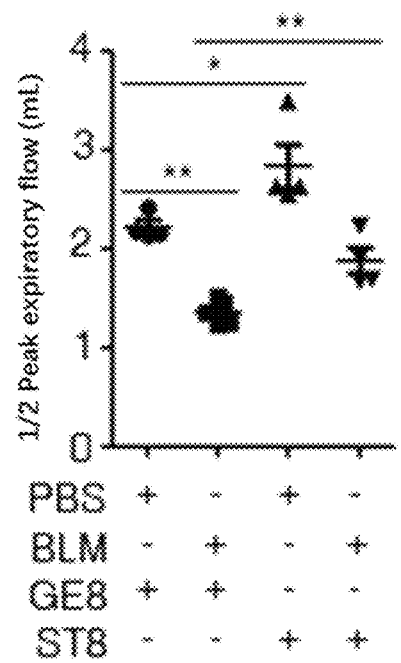
FIGS. 2A-2P show inhibition of ST8 (SEQ ID NO:25) on pulmonary fibrosis.
Figure 2B:
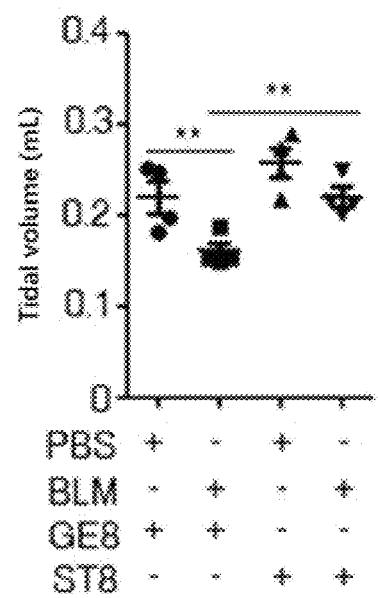
Figure 2C:
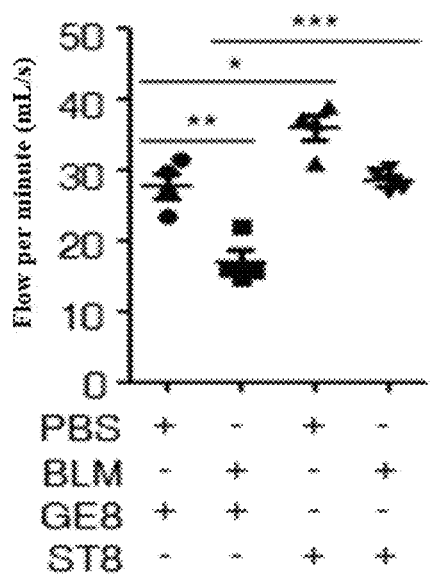
Figure 2D:
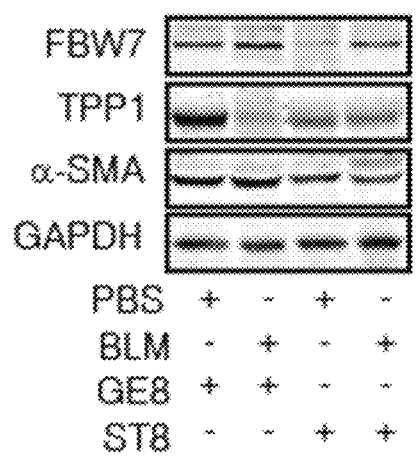
FIG. 2D illustrates the expression of FBW7, TPP1 and α-SMA in bleomycin-induced mice respectively perfused with ST8 and GE8.
Figure 2E:
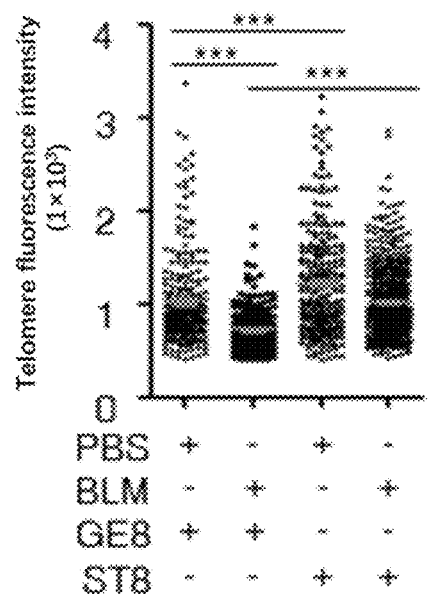
FIGS. 2E-F: telomere fluorescence intensity and proportion of lung alveolar (type II) epithelial stem cells in bleomycin-induced mice respectively perfused with ST8 and GE8.
Figure 2F:
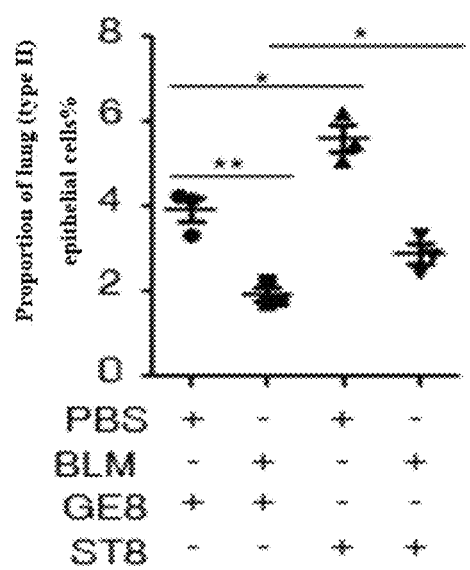
Figure 2G:
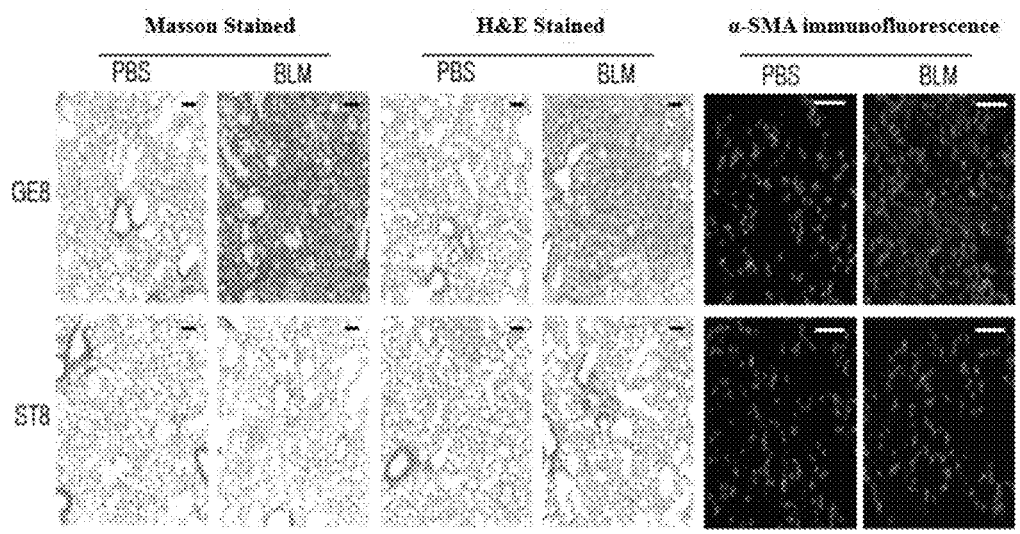
FIG. 2G: Masson and H&E staining results and expression of α-SMA in bleomycin-induced mice respectively perfused with YK21 and YK21h.
Figure 2H:
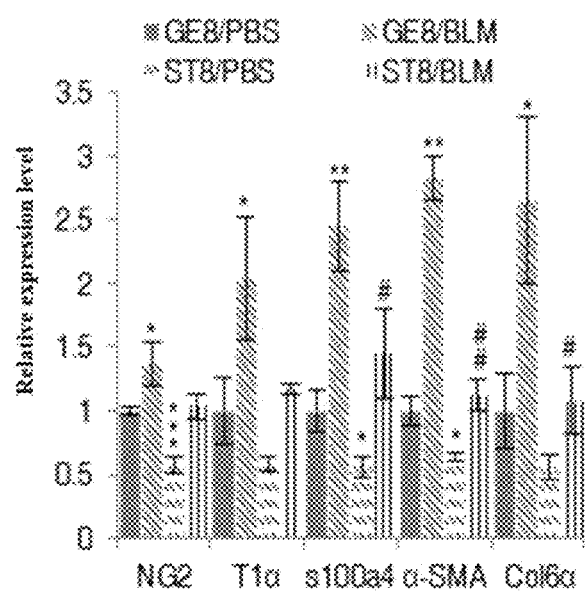
FIG. 2H illustrates the relative expression level of NG2, T1α, s100a4, α-SMA and col6a in bleomycin-induced mice respectively perfused with YK21 and YK21h.
Figure 2I:
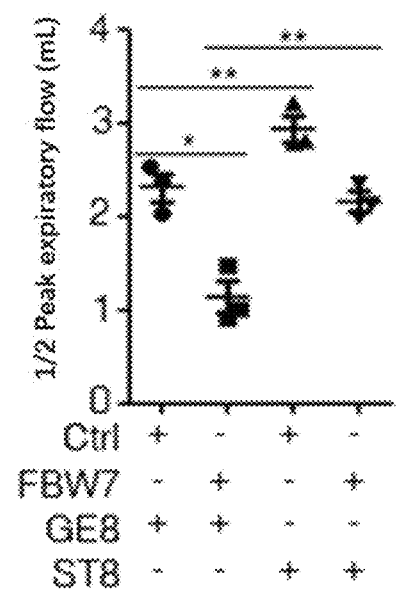
FIGS. 2I-K: expiratory influx, tidal and minute ventilation volumes of mice that were inoculated with FBW7 lentiviruses and respectively perfused with ST8 and GE8.
Figure 2J:
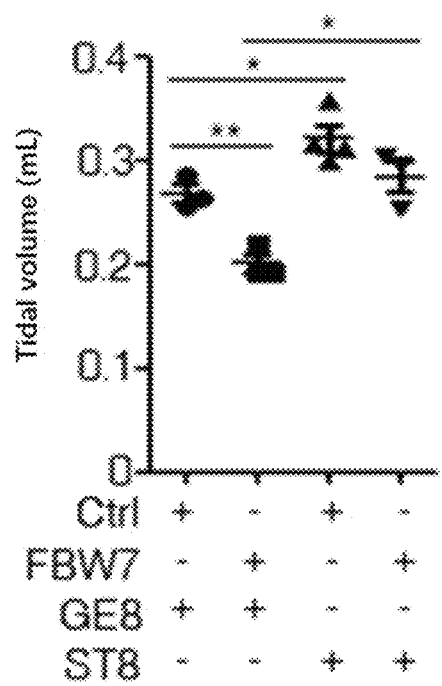
Figure 2K:
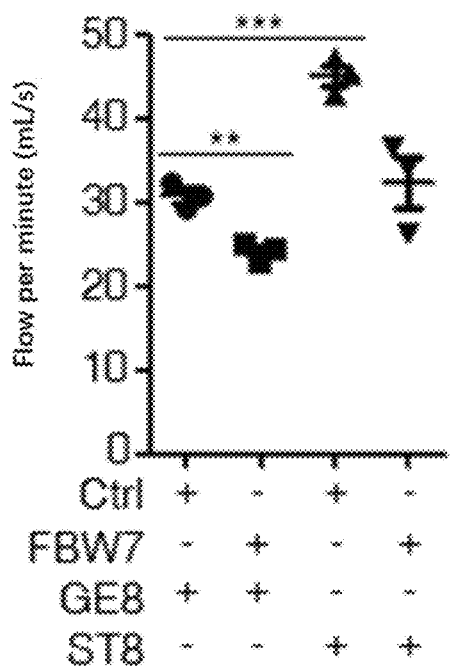
Figure 2L:
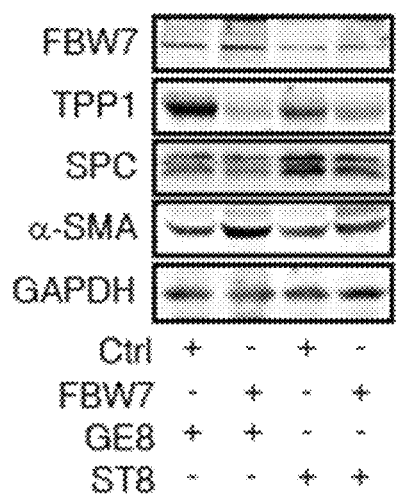
FIGS. 2L-N: mRNA expression of FBW7, TPP1, SPC, and α-SMA, telomere fluorescence intensity and proportion of SPC positive lung alveolar (type II) epithelial stem cells in mice that were that were inoculated with FBW7 lentiviruses and respectively perfused with ST8 and GE8.
Figure 2M:
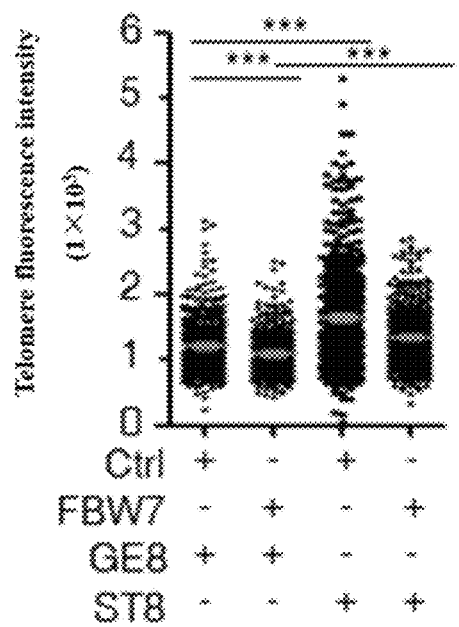
Figure 2N:
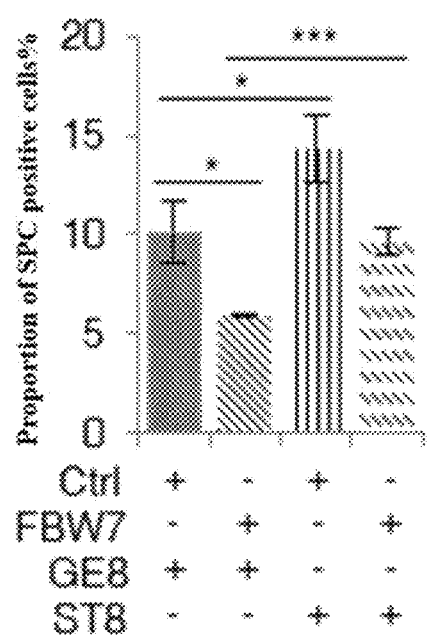
Figure 2O:
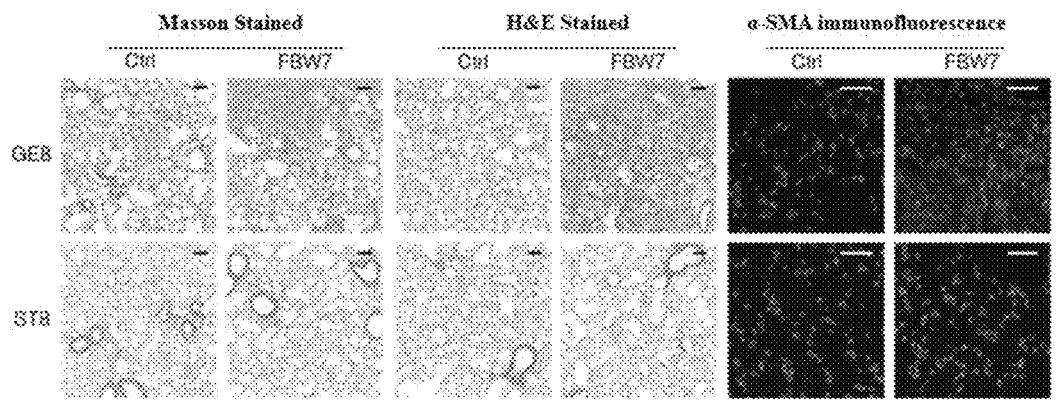
FIG. 2O: Masson and H&E staining results and expression of α-SMA in mice that were inoculated with FBW7 lentiviruses and respectively perfused with YK21 and YK21h.
Figure 2P:
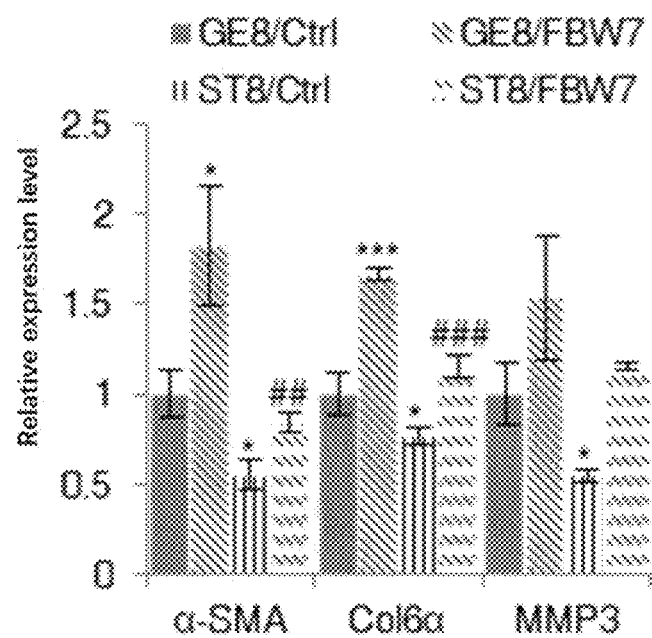

The results demonstrated that the shorter peptide ST8 merely consisting of 8 amino acids can alleviate the respiratory dysfunction in mice caused by bleomycin (FIGS. 2A-C), inhibit FBW7 and extend the telomere (FIG. 2D). In addition, ST8 also improved the proportion of lung type II epithelial cells (FIGS. 2E-F). Accordingly, ST8 showed inhibitory effect on the bleomycin-induced pulmonary fibrosis in mice (FIGS. 2G-H), and in the lung tissues with overexpression of FBW7, ST8 also played a significant role in alleviating the respiratory dysfunction in mice, the reduction in the expression of TPP1, the telomere shortening, the decrease in the proportion of type II epithelial cells and pulmonary fibrosis caused by the overexpression of FBW7 (FIGS. 2I-P).

EXAMPLE 4

Effect of DYK21 on Skin Aging, Weight Loss and Premature Death 48 2-4 month old wild mice were equally divided into four groups, and the hair in a 2 cm×2 cm region on the back of each of the mice was removed. Then two groups of mice did not undergo X-ray irradiation, and were respectively applied with DYK21 or a control peptide (DCTL1) at the dorsal skin region with hair removed for 7 consecutive days. The other two groups of mice were respectively applied with DYK21 or DCTL1 at the skin region with hair removed for 7 consecutive days, and subjected to 4-Gy irradiation with X rays in four hours after each application. The mice were photographed and weighed every day, and sacrificed on the $8^{th}$ day to collect the skin tissues.

Figure 3A:
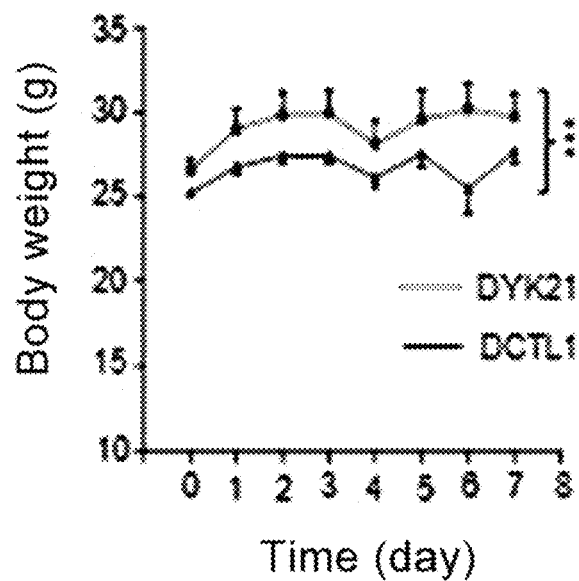
FIGS. 3A-G illustrate effect of DYK21 (SEQ ID NO:19, in D-amino acids) on body weight, skin thickness and fibrosis, and life span of mice under X-ray irradiation.
Figure 3B:
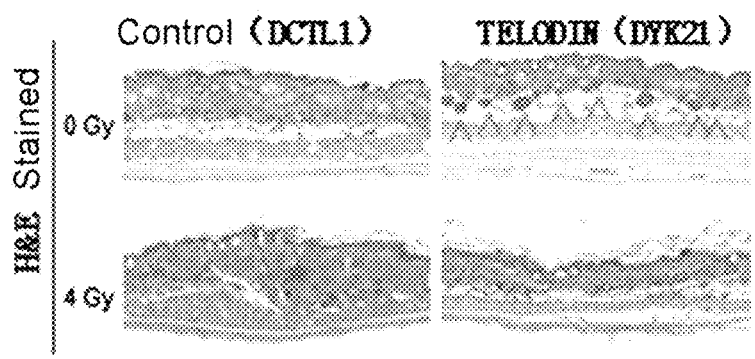
Figure 3C:
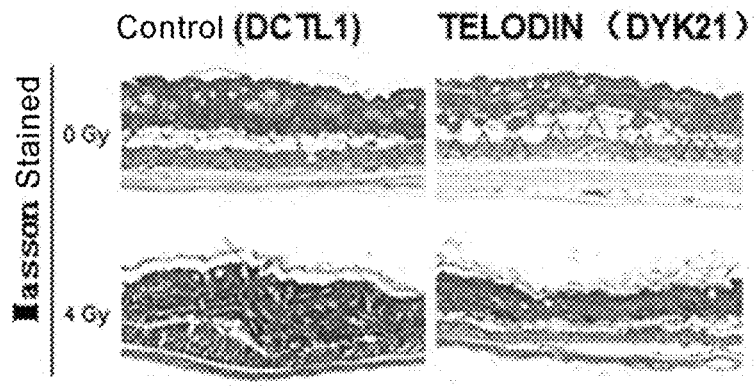
Figure 3D:
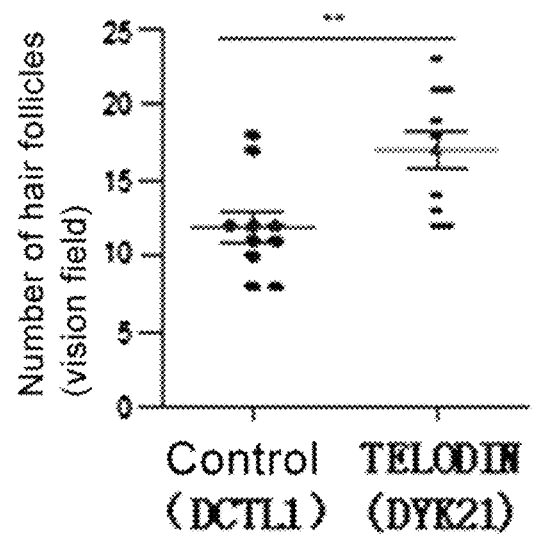
Figure 3E:
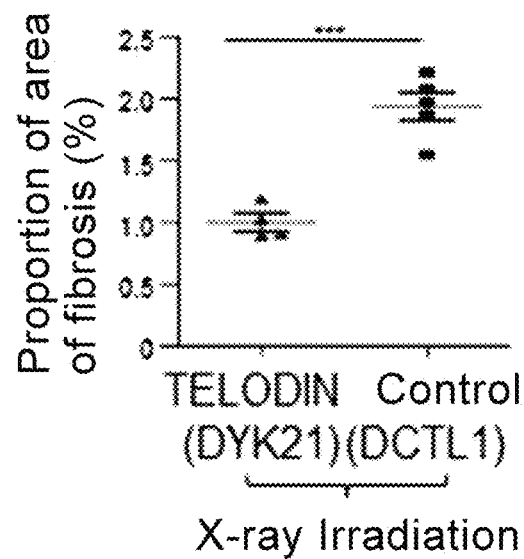
Figure 3F:
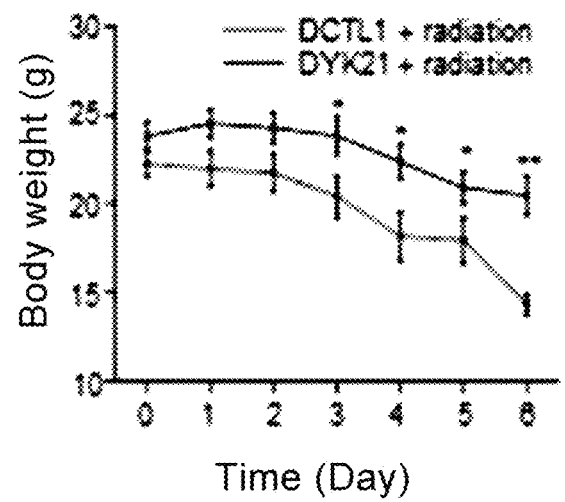
Figure 3G:
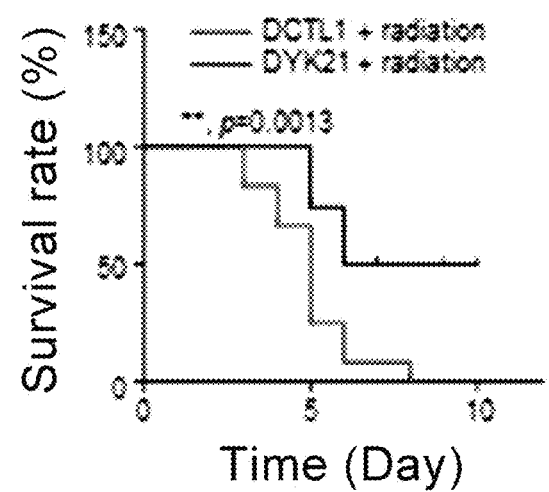

The results indicated that the death occurred in both of the two groups of mice undergoing 7 consecutive days of X-ray irradiation, but compared to the mice treated with DCTL1, the mice treated with DYK21 were larger in body weight (FIG. 3A) and had more hair follicles (FIGS. 3B-D, marked with "arrow"). In addition, DYK21 showed significant inhibitory effect on the skin damage and fibrous tissue proliferation in mice caused by X-ray irradiation (FIGS. 3B-C, marked with "star"). As shown in FIG. 3E, the application of DYK21 resulted in a smaller fibrosis area. Compared to DCTL1, DYK21 inhibited the weight loss caused by X-ray irradiation, alleviated the acute death to some extent and prolonged the life of some mice.

EXAMPLE 5

Figure 4A:
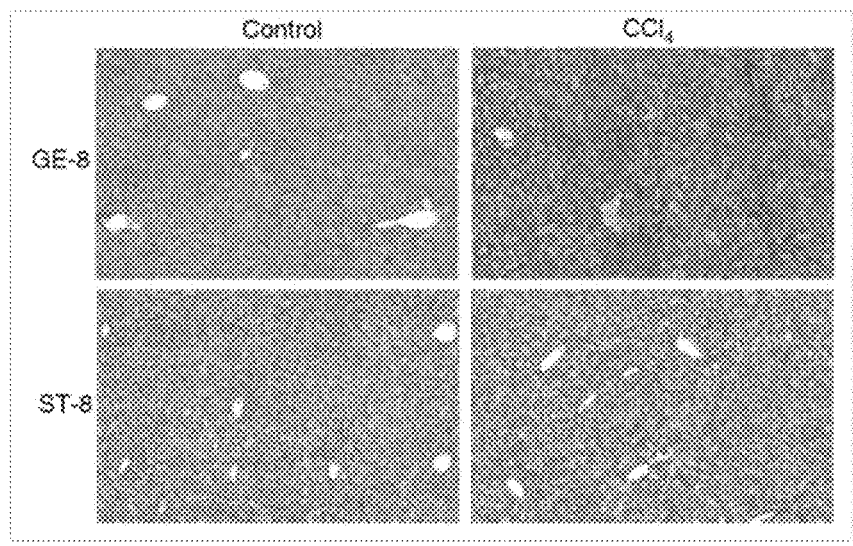
FIGS. 4A-B illustrate the inhibitory effect of DST8 on carbon tetrachloride-induced liver fibrosis using Masson staining and Western blot.
Figure 4B:
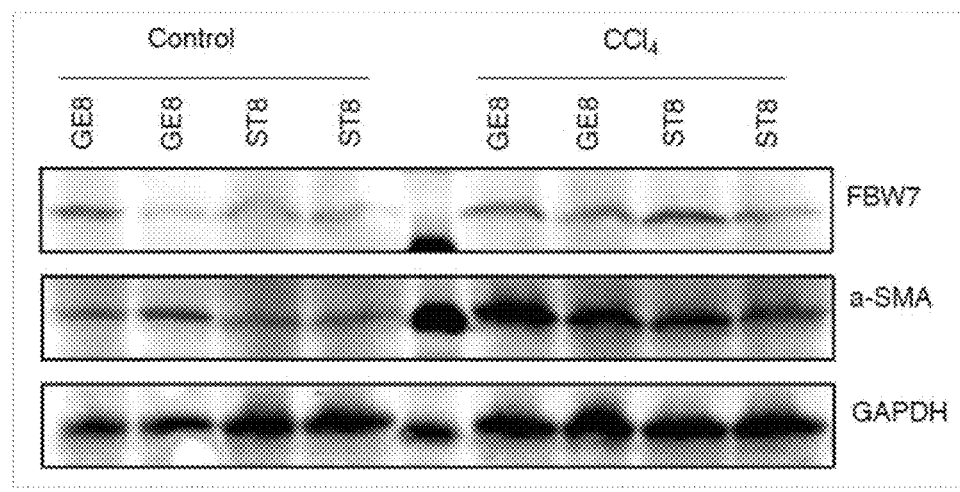

Effect of DST8 on Liver Fibrosis Caused by Drugs 12 6 week old wild female C57BL/6 mice were equally divided into four groups, where two groups of mice were intraperitoneally injected with a solution of 10% carbon tetrachloride in olive oil three times a week (on every Monday, Wednesday and Friday, 5 μL per gram of body weight), and the other two groups of mice were intraperitoneally injected with an equal amount of olive oil as control. The two groups injected with carbon tetrachloride were intraperitoneally injected with DST8 (SerArgAsnGlyThrGluGluThr, in D-amino acids), 1 mg per kilogram of body weight) and GE8 (SEQ ID NO:24), respectively, 4 hours before the first injection of carbon tetrachloride in each week. The two control groups were also intraperitoneally injected with DST8 (1 mg per kilogram of body weight) and GE8, respectively, 4 hours before the first injection of olive oil in each week. After 4 consecutive weeks of administration, the liver was isolated, embedded with paraffin, sectioned and subjected to Masson staining and Western Blot analysis. The results showed that the intraperitoneal injection of DST8 targeting FBW7 can significantly inhibit the liver fibrosis caused by carbon tetrachloride (FIG. 4A-B).

What is claimed is:

1. A peptide for inhibiting telomere damage, wherein the peptide is ST8 (SEQ ID NO:25), YK21 (SEQ ID NO:1), DYK21 (SEQ ID NO:19) or DKY21 (SEQ ID NO:20).

2. The peptide of claim 1, wherein the ST8 has a molecular weight of 892.88.

3. The peptide of claim 1, wherein the YK21 has a molecular weight of 2619.96; the DYK21 a molecular weight of 2619.94; and the DKY21 has a molecular weight of 2619.96.

4. A method for treating a telomere dysfunction-associated disease in a patient in need thereof, comprising:
administering the peptide of claim 1 to the patient.

5. The method of claim 4, wherein the telomere dysfunction-associated disease is a disease caused by telomere damage or telomere shortening, and the disease caused by telomere damage or telomere shortening is selected from the group consisting of pulmonary fibrosis, myocardial fibrosis, liver fibrosis, renal fibrosis, bone marrow fibrosis, hematopoietic stem cell reduction, anemia, immune dysfunction, thymic fibrosis, ovarian fibrosis, premature ovarian failure, bone and joint fibrosis, osteoporosis, vascular fibrosis, neurodegenerative damage, diabetes, aging and degeneration of tissues and organs, tumors and age-related chronic obstructive pulmonary disease.

6. The method of claim 5, wherein the aging of tissues and organs comprises skin aging, comprising skin wrinkles, dyskeratosis, hair regeneration disorder, hair loss and alopecia.

7. The method of claim 5, wherein the telomere damage leading to the aging and degeneration of tissues and organs, pulmonary fibrosis, myocardial fibrosis, liver fibrosis, renal fibrosis, bone marrow fibrosis, thymic fibrosis, ovarian fibrosis, bone and joint fibrosis and vascular fibrosis is induced by environmental stress and stress.

* * * * *

SEQUENCE LISTING

<160> NUMBER OF SEQ ID NOS: 27

<210> SEQ ID NO 1
<211> LENGTH: 21
<212> TYPE: PRT
<213> ORGANISM: Artificial Sequence
<220> FEATURE:
<223> OTHER INFORMATION: synthetic

<400> SEQUENCE: 1

Tyr Gly Arg Lys Lys Arg Arg Glu Arg Arg Gly Ser Arg Asn Gly
1               5                   10                  15

Thr Glu Glu Thr Lys
            20

<210> SEQ ID NO 2
<211> LENGTH: 21
<212> TYPE: PRT
<213> ORGANISM: Artificial Sequence
<220> FEATURE:
<223> OTHER INFORMATION: synthetic

<400> SEQUENCE: 2

Tyr Gly Arg Lys Lys Arg Arg Glu Arg Arg Gly Glu Arg Asn Gly
1               5                   10                  15

Thr Glu Glu Thr Lys
            20

<210> SEQ ID NO 3
<211> LENGTH: 32
<212> TYPE: PRT
<213> ORGANISM: Artificial Sequence
<220> FEATURE:
<223> OTHER INFORMATION: synthetic

<400> SEQUENCE: 3

Tyr Gly Arg Lys Lys Arg Arg Glu Arg Arg Gly Ser Arg Asn Gly
1               5                   10                  15

Thr Glu Glu Thr Lys Leu Leu Val Leu Asp Phe Asp Val Asp Met Lys
            20                  25                  30

<210> SEQ ID NO 4
<211> LENGTH: 26
<212> TYPE: PRT
<213> ORGANISM: Artificial Sequence
<220> FEATURE:

<223> OTHER INFORMATION: synthetic

<400> SEQUENCE: 4

Tyr Gly Arg Lys Lys Arg Arg Glu Arg Arg Gly Ser Thr Asp Arg
1               5                   10                  15
Thr Leu Lys Val Trp Asn Ala Glu Thr Gly
            20                  25

<210> SEQ ID NO 5
<211> LENGTH: 26
<212> TYPE: PRT
<213> ORGANISM: Artificial Sequence
<220> FEATURE:
<223> OTHER INFORMATION: synthetic

<400> SEQUENCE: 5

Tyr Gly Arg Lys Lys Arg Arg Glu Arg Arg Gly Glu Leu Lys Ser
1               5                   10                  15
Pro Lys Val Leu Lys Gly His Asp Asp His
            20                  25

<210> SEQ ID NO 6
<211> LENGTH: 19
<212> TYPE: PRT
<213> ORGANISM: Artificial Sequence
<220> FEATURE:
<223> OTHER INFORMATION: synthetic

<400> SEQUENCE: 6

Tyr Gly Arg Lys Lys Arg Arg Glu Arg Arg Gly Pro Asn Lys His
1               5                   10                  15
Gln Ser Ala

<210> SEQ ID NO 7
<211> LENGTH: 27
<212> TYPE: PRT
<213> ORGANISM: Artificial Sequence
<220> FEATURE:
<223> OTHER INFORMATION: synthetic

<400> SEQUENCE: 7

Tyr Gly Arg Lys Lys Arg Arg Glu Arg Arg Ala Val Thr Gly Lys
1               5                   10                  15
Cys Leu Arg Thr Leu Val Gly His Thr Gly Gly
            20                  25

<210> SEQ ID NO 8
<211> LENGTH: 19
<212> TYPE: PRT
<213> ORGANISM: Artificial Sequence
<220> FEATURE:
<223> OTHER INFORMATION: synthetic

<400> SEQUENCE: 8

Tyr Gly Arg Lys Lys Arg Arg Glu Arg Arg Gly Ala Tyr Asp Phe
1               5                   10                  15
Met Val Lys

<210> SEQ ID NO 9
<211> LENGTH: 29
<212> TYPE: PRT
<213> ORGANISM: Artificial Sequence
<220> FEATURE:
<223> OTHER INFORMATION: synthetic

<400> SEQUENCE: 9

Tyr Gly Arg Lys Lys Arg Arg Glu Arg Arg Lys Glu Glu Gly Ile
1               5                   10                  15

Asp Glu Pro Leu His Ile Lys Arg Arg Lys Val Ile Lys
            20                  25

<210> SEQ ID NO 10
<211> LENGTH: 18
<212> TYPE: PRT
<213> ORGANISM: Artificial Sequence
<220> FEATURE:
<223> OTHER INFORMATION: synthetic

<400> SEQUENCE: 10

Tyr Gly Arg Lys Lys Arg Arg Glu Arg Arg Gly His Thr Ser Thr
1               5                   10                  15

Val Ala

<210> SEQ ID NO 11
<211> LENGTH: 21
<212> TYPE: PRT
<213> ORGANISM: Artificial Sequence
<220> FEATURE:
<223> OTHER INFORMATION: synthetic

<400> SEQUENCE: 11

Tyr Gly Arg Lys Lys Arg Arg Glu Arg Arg Lys Arg Arg Arg Thr
1               5                   10                  15

Gly Gly Ser Leu Arg
            20

<210> SEQ ID NO 12
<211> LENGTH: 19
<212> TYPE: PRT
<213> ORGANISM: Artificial Sequence
<220> FEATURE:
<223> OTHER INFORMATION: synthetic

<400> SEQUENCE: 12

Tyr Gly Arg Lys Lys Arg Arg Glu Arg Arg Arg Asn Gly Thr Glu
1               5                   10                  15

Glu Thr Lys

<210> SEQ ID NO 13
<211> LENGTH: 20
<212> TYPE: PRT
<213> ORGANISM: Artificial Sequence
<220> FEATURE:
<223> OTHER INFORMATION: synthetic

<400> SEQUENCE: 13

Tyr Gly Arg Lys Lys Arg Arg Glu Arg Arg Gly Ser Asn Gly Thr
1               5                   10                  15

Glu Glu Thr Lys
            20

<210> SEQ ID NO 14
<211> LENGTH: 20
<212> TYPE: PRT
<213> ORGANISM: Artificial Sequence
<220> FEATURE:
<223> OTHER INFORMATION: synthetic

```
<400> SEQUENCE: 14

Tyr Gly Arg Lys Lys Arg Arg Glu Arg Arg Gly Ser Arg Gly Thr
1               5                   10                  15

Glu Glu Thr Lys
            20

<210> SEQ ID NO 15
<211> LENGTH: 20
<212> TYPE: PRT
<213> ORGANISM: Artificial Sequence
<220> FEATURE:
<223> OTHER INFORMATION: synthetic

<400> SEQUENCE: 15

Tyr Gly Arg Lys Lys Arg Arg Glu Arg Arg Gly Ser Arg Asn Gly
1               5                   10                  15

Thr Glu Glu Thr
            20

<210> SEQ ID NO 16
<211> LENGTH: 19
<212> TYPE: PRT
<213> ORGANISM: Artificial Sequence
<220> FEATURE:
<223> OTHER INFORMATION: synthetic

<400> SEQUENCE: 16

Tyr Gly Arg Lys Lys Arg Arg Glu Arg Arg Gly Ser Arg Asn Gly
1               5                   10                  15

Thr Glu Glu

<210> SEQ ID NO 17
<211> LENGTH: 20
<212> TYPE: PRT
<213> ORGANISM: Artificial Sequence
<220> FEATURE:
<223> OTHER INFORMATION: synthetic

<400> SEQUENCE: 17

Tyr Gly Arg Lys Lys Arg Arg Glu Arg Arg Gly Ser Arg Asn Gly
1               5                   10                  15

Thr Glu Thr Lys
            20

<210> SEQ ID NO 18
<211> LENGTH: 21
<212> TYPE: PRT
<213> ORGANISM: Artificial Sequence
<220> FEATURE:
<223> OTHER INFORMATION: synthetic

<400> SEQUENCE: 18

Tyr Gly Arg Lys Lys Arg Arg Glu Arg Arg Gly Asp Arg Asn Gly
1               5                   10                  15

Thr Glu Glu Thr Lys
            20

<210> SEQ ID NO 19
<211> LENGTH: 21
<212> TYPE: PRT
<213> ORGANISM: Artificial Sequence
<220> FEATURE:
<223> OTHER INFORMATION: synthetic
```

```
<400> SEQUENCE: 19

Tyr Gly Arg Lys Lys Arg Glu Arg Arg Gly Ser Arg Asn Gly
 1               5                  10                  15

Thr Glu Glu Thr Lys
             20

<210> SEQ ID NO 20
<211> LENGTH: 21
<212> TYPE: PRT
<213> ORGANISM: Artificial Sequence
<220> FEATURE:
<223> OTHER INFORMATION: synthetic

<400> SEQUENCE: 20

Lys Thr Glu Glu Thr Gly Asn Arg Ser Gly Arg Arg Gln Arg Arg
 1               5                  10                  15

Lys Lys Arg Gly Tyr
             20

<210> SEQ ID NO 21
<211> LENGTH: 21
<212> TYPE: PRT
<213> ORGANISM: Artificial Sequence
<220> FEATURE:
<223> OTHER INFORMATION: synthetic

<400> SEQUENCE: 21

Lys Thr Glu Glu Thr Gly Asn Arg Ser Gly Arg Arg Gln Arg Arg
 1               5                  10                  15

Lys Lys Arg Gly Tyr
             20

<210> SEQ ID NO 22
<211> LENGTH: 10
<212> TYPE: PRT
<213> ORGANISM: Artificial Sequence
<220> FEATURE:
<223> OTHER INFORMATION: synthetic

<400> SEQUENCE: 22

Gly Ser Arg Asn Gly Thr Glu Glu Thr Lys
 1               5                  10

<210> SEQ ID NO 23
<211> LENGTH: 9
<212> TYPE: PRT
<213> ORGANISM: Artificial Sequence
<220> FEATURE:
<223> OTHER INFORMATION: synthetic

<400> SEQUENCE: 23

Gly Ser Arg Asn Gly Thr Glu Glu Thr
 1               5

<210> SEQ ID NO 24
<211> LENGTH: 8
<212> TYPE: PRT
<213> ORGANISM: Artificial Sequence
<220> FEATURE:
<223> OTHER INFORMATION: synthetic

<400> SEQUENCE: 24

Gly Ser Arg Asn Gly Thr Glu Glu
 1               5
```

```
<210> SEQ ID NO 25
<211> LENGTH: 8
<212> TYPE: PRT
<213> ORGANISM: Artificial Sequence
<220> FEATURE:
<223> OTHER INFORMATION: synthetic

<400> SEQUENCE: 25

Ser Arg Asn Gly Thr Glu Glu Thr
1               5

<210> SEQ ID NO 26
<211> LENGTH: 7
<212> TYPE: PRT
<213> ORGANISM: Artificial Sequence
<220> FEATURE:
<223> OTHER INFORMATION: synthetic

<400> SEQUENCE: 26

Ser Arg Asn Gly Thr Glu Glu
1               5

<210> SEQ ID NO 27
<211> LENGTH: 22
<212> TYPE: PRT
<213> ORGANISM: Artificial Sequence
<220> FEATURE:
<223> OTHER INFORMATION: synthetic

<400> SEQUENCE: 27

Ala Cys Thr Gly Ser Thr Gln His Gln Cys Gly Gly Gly Gly Ser Arg
1               5                   10                  15

Asn Gly Thr Glu Glu Thr
            20
```